United States Patent
Fujiwara

(10) Patent No.: US 9,974,511 B2
(45) Date of Patent: May 22, 2018

(54) MEDICAL IMAGING APPARATUS AND MEDICAL IMAGING METHOD

(71) Applicant: TOSHIBA MEDICAL SYSTEMS CORPORATION, Otawara-Shi (JP)

(72) Inventor: Megumu Fujiwara, Sakura (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 82 days.

(21) Appl. No.: 15/074,411

(22) Filed: Mar. 18, 2016

(65) Prior Publication Data
US 2016/0361038 A1  Dec. 15, 2016

(30) Foreign Application Priority Data
Jun. 9, 2015 (JP) ................................. 2015-116250

(51) Int. Cl.
| | | |
|---|---|---|
| G06K 9/00 | (2006.01) | |
| A61B 6/00 | (2006.01) | |
| A61B 6/03 | (2006.01) | |
| G06T 7/00 | (2017.01) | |

(52) U.S. Cl.
CPC ............ *A61B 6/5264* (2013.01); *A61B 6/032* (2013.01); *A61B 6/463* (2013.01); *A61B 6/466* (2013.01); *A61B 6/505* (2013.01); *G06T 7/0012* (2013.01)

(58) Field of Classification Search
None
See application file for complete search history.

(56) References Cited

U.S. PATENT DOCUMENTS

| | | | |
|---|---|---|---|
| 9,280,718 B2* | 3/2016 | Claude | ................. A61B 5/055 |
| 2012/0226141 A1* | 9/2012 | Shinoda | ................. G01R 33/48 |
| | | | 600/419 |
| 2013/0223703 A1* | 8/2013 | Fujisawa | ............... G06F 19/321 |
| | | | 382/128 |

FOREIGN PATENT DOCUMENTS

JP      2013-172815      9/2013

* cited by examiner

*Primary Examiner* — Shervin Nakhjavan
(74) *Attorney, Agent, or Firm* — Oblon, McClelland, Maier & Neustadt, L.L.P.

(57) ABSTRACT

A medical imaging apparatus according to a present embodiment includes processing circuitry. The processing circuitry obtains pieces of medical image data, the pieces each being generated in each of multiple time phases and each including bone information. The processing circuitry sets first regions each being included in each of the pieces. The processing circuitry generates pieces of corrected medical image data by aligning the pieces of medical image data so that the first regions are substantially a same position. The processing circuitry specifies second regions each corresponding to a bone moving in the pieces of the corrected medical image data. The processing circuitry displays the second regions so as to be recognized on a display.

14 Claims, 7 Drawing Sheets

CT VOLUME DATA IN THREE PHASES

CT VOLUME DATA IN THREE PHASES

3D SHADOW REGION DATA IN THREE PHASES

3D NON-COMMON REGION DATA IN THREE PHASES

3D CORRECTED REGION DATA IN THREE PHASES

3D RETURNED REGION DATA IN THREE PHASES

POSITION CHANGED VOLUME DATA IN THREE PHASES

4D REPRESENTATION BASED ON 3D IMAGE DATA

3D COMMON REGION DATA IN THREE PHASES

POSITION CHANGED VOLUME DATA IN THREE PHASES

4D REPRESENTATION BASED ON 3D IMAGE DATA

4D REPRESENTATION BASED ON 3D SPECIFIED BONE REGION

4D REPRESENTATION BASED ON 3D IMAGE DATA INCLUDING MAPPING

4D REPRESENTATION BASED ON 3D IMAGE DATA INCLUDING MAPPING

CT-2D DATA IN THREE PHASES

MEDICAL IMAGING APPARATUS AND MEDICAL IMAGING METHOD

CROSS-REFERENCE TO RELATED APPLICATION

This application is based upon and claims the benefit of priority from Japanese Patent Application No. 2015-116250, filed on Jun. 9, 2015, the entire contents of which are incorporated herein by reference.

FIELD

An embodiment as an aspect of the present invention relates to a medical imaging apparatus and a medical imaging method that perform data processing on data including information on bones.

BACKGROUND

A medical imaging apparatus displays 3D image data based on volume data (3D (dimensional) data) collected by a medical image generating apparatus (medical diagnostic imaging apparatus). The medical image generating apparatus is, for example, an X-ray CT (computed tomography) scanner, an MRI (magnetic resonance imaging) apparatus, a diagnostic X-ray apparatus, and ultrasonic diagnostic equipment.

In recent years, techniques for 4D representation of pieces of 3D image data have been significantly advanced, the pieces each being generated in each of multiple time phases and generated by a medical image generating apparatus so as to have a high time resolution in addition to a three-dimensional spatial resolution. Accordingly, a region including movable parts (joints) such as a wrist and an ankle is scanned using, for example, an X-ray CT apparatus so as to generate pieces of CT volume data in multiple time phases while the movable parts are moved by bending, stretching, adduction, abduction, incycloduction, and excycloduction. Subsequently, movements of bones in or around the movable parts are shown to an operator by 4D representation provided using the pieces of 3D image data based on the pieces of the CT volume data. Such a technique has been generally used.

In a multi-slice X-ray CT apparatus, projection data can be obtained over a wider region by a single scan as detecting elements increase in number in a slicing direction (row direction) of a detector. In other words, dynamic volume scanning sequentially performed using the multi-slice X-ray CT apparatus can generate pieces of CT volume data in multiple time phases with a high frame rate. Thus, an operator can evaluate movements of bones through 4D representation within a unit time.

According to a disclosed technique in this technical field, a target bone (a bone region indicating a bone shadow region) is specified, position information on the bone in a first phase piece of volume data and position information on the bone in a second phase piece of volume data are determined, and 4D representation is provided based on the position information so as to show sequential changes of relative positions of other bones with respect to the target bone.

In 4D representation of prior art, however, many bones are moved in a complicated manner according to movements of movable parts, making it difficult for an operator to recognize the target bone from the 4D representation.

Moreover, in the 4D representation showing the sequential changes of the relative positions of the other bones with respect to the target bone, the target bone needs to be specified in advance on an image. Thus, if the target bone is not recognizable, the operator specifies target bone candidates one by one, lets the apparatus execute multiple 4D representations each showing sequential changes of relative positions of other bones with respect to the fixed target bone candidate, and has to visually confirm a target bone which is one of the target bone candidates while comparing the executed 4D representations.

An object of the present invention is to provide a medical imaging apparatus and a medical imaging method that can improve efficiency of image diagnosis performed by an operator in 4D representation.

BRIEF DESCRIPTION OF THE DRAWINGS

In accompanying drawings.

DETAILED DESCRIPTION

A medical imaging apparatus and a medical imaging method according to a present embodiment will be described below with reference to accompanying drawings.

The medical imaging apparatus according to the present embodiment includes processing circuitry. The processing circuitry obtains pieces of medical image data, the pieces each being generated in each of multiple time phases and each including bone information. The processing circuitry sets first regions each being included in each of the pieces. The processing circuitry generates pieces of corrected medical image data by aligning the pieces of medical image data so that the first regions are substantially a same position. The processing circuitry specifies second regions each corresponding to a bone moving in the pieces of the corrected medical image data. The processing circuitry displays the second regions so as to be recognized on a display.

Figure 1:
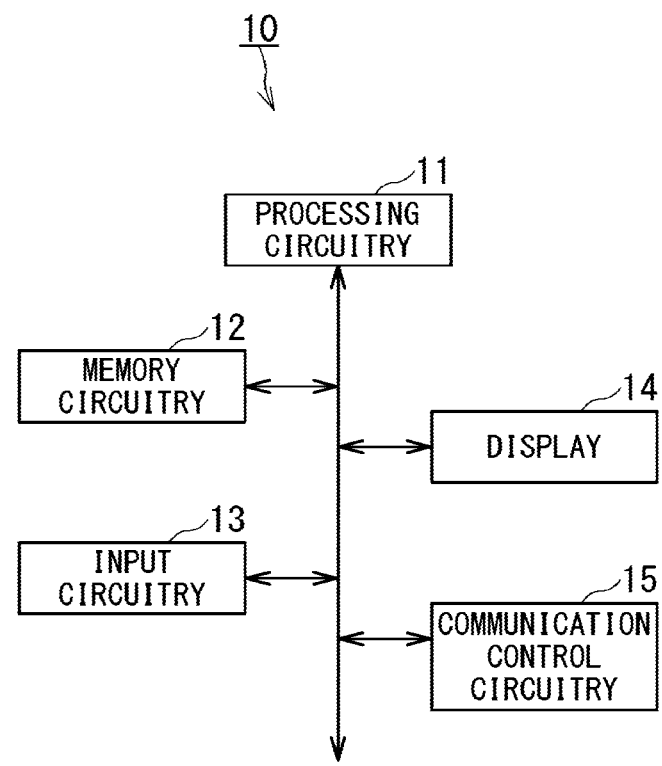
FIG. 1 is a schematic diagram showing a hardware configuration of a medical imaging apparatus according to a present embodiment.

FIG. 1 is a schematic diagram showing a hardware configuration of the medical imaging apparatus according to the present embodiment.

FIG. 1 shows a medical imaging apparatus 10 according to the present embodiment. The medical imaging apparatus 10 may be provided on a medical imaging system that connects various apparatuses including a medical image generating apparatus (medical diagnostic imaging apparatus, not shown), a medical image management apparatus (image server, not shown), and an image interpretation terminal (not shown) via a network. The medical image generating apparatus generates pieces of medical image data (hereinafter called "medical images") in multiple time phases. The medical image management apparatus stores and manages the medical images. The image interpretation terminal receives the medical images stored in the medical image management apparatus and displays the data so as to allow image interpretation by a doctor.

In the following example, functions are performed by the medical imaging apparatus 10 alone. These functions may be performed by the overall medical imaging system where the functions are shared among the apparatuses constituting the medical imaging system.

The medical imaging apparatus 10 includes processing circuitry 11, memory circuitry 12, input circuitry 13, a display 14, and communication control circuitry 15.

The processing circuitry 11 reads various control programs stored in the memory circuitry 12 and performs various operations. Furthermore, the processing circuitry 11 collectively controls processing operations in the circuitry 12 to the circuitry 15.

The processing circuitry 11 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 11 reads programs stored in the memory circuitry 12 or directly implemented in the processing circuitry 11 and executes these programs.

The processing circuitry 11 may be a single processing circuit or a combination of multiple processing circuits. In the latter case, the memory circuitry 12 includes multiple memory circuits each storing an element of a program, each of the multiple memory circuits is provided for each of the multiple circuits. Alternatively, the memory circuitry 12 includes a single memory circuit storing the program, the single memory circuit is provided for the multiple circuits.

The memory circuitry 12 is composed of semiconductor memory devices such as a random access memory (RAM) and a flash memory, a hard disk, and an optical disk. The memory circuitry 12 may be composed of a universal serial bus (USB) memory and portable media such as a digital video disk (DVD). The memory circuitry 12 stores data necessary for executing a control program used in the processing circuitry 11, data received from, for example, a medical image generating apparatus (not shown) or a medical image management apparatus (not shown) through the communication control circuitry 15 or a portable medium, and data generated by the processing circuitry 11. Moreover, an OS may include a graphic user interface (GUI) that frequently provides, for an operator, graphic display of information on the display 14 and enables basic operations through the input circuitry 13.

The input circuitry 13 is composed of a keyboard, a mouse, and so on. When an operator operates the input circuitry 13, the input circuitry 13 generates an operation signal corresponding to the operation and then outputs the signal to the processing circuitry 11. The input circuitry 13 may include a touch panel integrated with the display 14.

The display 14 is a display device, for example, a liquid crystal display (LCD). In response to an instruction from the processing circuitry 11, the display 14 shows various operation screens and kinds of display information such as pieces of 3D image data (hereinafter called "3D images") in multiple time phases generated by the processing circuitry 11. The display 14 can provide 4D representation (sequentially in the time phases) using the 3D images generated in multiple time phases and generated by the processing circuitry 11.

The communication control circuitry 15 is composed of, for example, connectors for parallel connection specifications or serial connection specifications. The communication control circuitry 15 transmits and receives information to and from an external apparatus on a network. For example, the communication control circuitry 15 communicates with the external apparatus such that pieces of volume data (hereinafter called "volumes") in multiple time phases is received from the medical image generating apparatus (not shown) or the medical image management apparatus (not shown) and the 3D images in multiple time phases generated by the processing circuitry 11 is transmitted to the medical image generating apparatus (not shown) or the image interpretation terminal (not shown).

Figure 2:
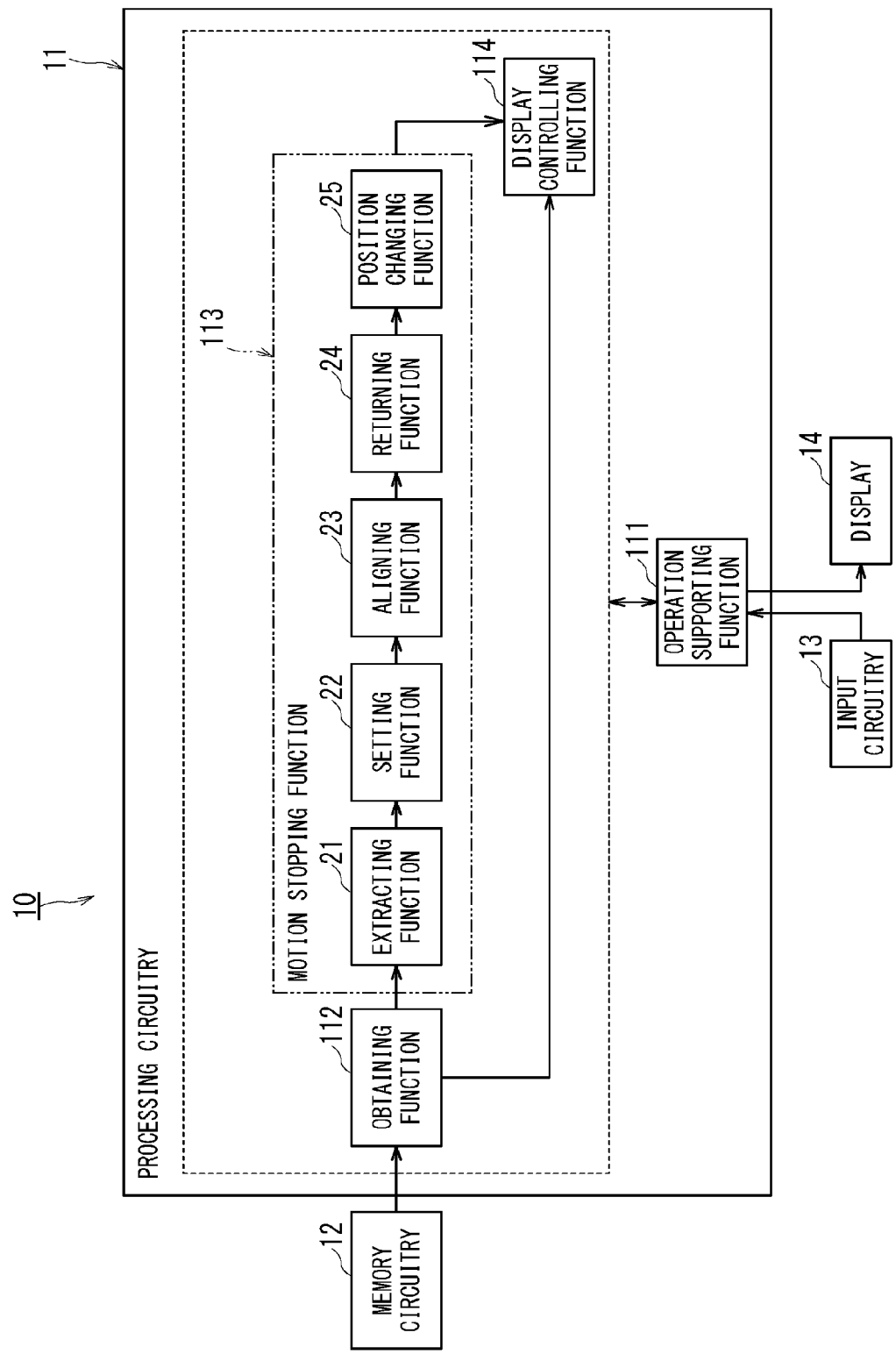
FIG. 2 is a block diagram showing functions of the medical imaging apparatus according to the present embodiment.

FIG. 2 is a block diagram showing functions of the medical imaging apparatus 10 according to the present embodiment.

The execution of the program by the processing circuitry 11 causes the medical imaging apparatus 10 to perform an operation supporting function 111, an obtaining (reading) function 112, a motion stopping function 113, and a display controlling function 114.

In this example, the functions 111 to 114 of the medical imaging apparatus 10 are performed as software. Some or all of the functions 111 to 114 may be provided as hardware in the medical imaging apparatus 10.

The operation supporting function 111 is a user interface, for example, a graphic user interface (GUI) that frequently provides, for an operator, graphic display of information on the display 14 and enables basic operations through the input circuitry 13.

The obtaining function 112 obtains, from the memory circuitry 12, the medical images as volumes (3D data), the medical images each being generated in multiple time phases and each including bone information. The medical images are obtained by scanning a region including movable parts such as a wrist joint, an ankle joint, an elbow joint, and a knee joint while moving the movable parts.

Each of the volumes is obtained by scanning through, for example, an X-ray CT apparatus and a magnetic resonance imaging (MRI) apparatus. In the following explanation, each of the volumes is generated by an X-ray CT apparatus. Each of CT volumes contains CT values for voxels in a 3D array.

Figure 3:
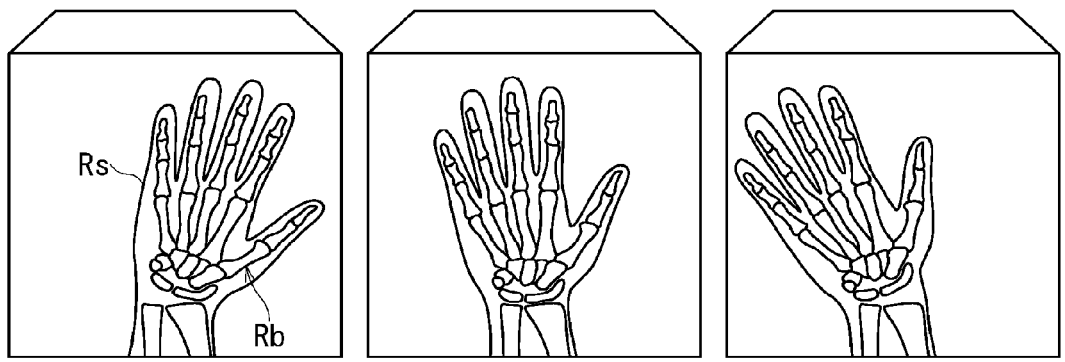
FIG. 3 is a diagram showing CT volume data obtained in three phases by scanning radial flexion and ulnar flexion of a wrist.

FIG. 3 is a diagram showing the CT volumes obtained in three phases by scanning radial flexion and ulnar flexion of a wrist. Each of the CT volumes shown in FIG. 3 roughly includes a bone region Rb indicating bones (including cartilage) and a soft tissue region Rs containing elements such as other skins and muscles.

Referring to FIG. 2 again, in the motion stopping function 113, the CT volumes obtained by the obtaining function 112 serve as the medical images of a subject to be stopped. Subsequently, the motion stopping function 113 sets first regions each included in each of the CT volumes, and aligns the CT volumes so that the first regions are substantially at a same position. In the result, the motion stopping function 113 generates pieces of corrected CT volume data (hereinafter called "corrected CT volumes") in multiple time phases.

The motion stopping function 113 sets at least one kind of bone as the first regions of the corresponding CT volumes, and performs alignment (rotation and translation) of the CT volumes so as to stop a motion of a first region which is the at least one kind of bone. The motion is generated in playing images based on the CT volumes in chronological order. First, the motion stopping function 113 performs alignment of the CT volumes so as to stop a motion of the first region (at least one kind of bone) directly set in response to an input signal from the input circuitry 13. Second, the motion stopping function 113 sets regions of interest in the corresponding CT volumes in response to an input signal of the input circuitry 13 so as to indirectly set the first regions in the corresponding regions of interest, and then the motion stopping function 113 performs alignment of the CT volumes so as to stop a motion of a region of interest. The setting of the first regions and the placement of the regions of interest for setting the first regions are performed on, for example, images based on the volumes shown in FIG. 3.

Third, the motion stopping function 113 performs alignment (rotation and translation) of the CT volumes so as to stop a motion of the first region (shadow region) included in each of the CT volumes. In other words, the motion stopping function 113 performs alignment on the overall each of the CT volumes so as to align non-common regions each being included in each of the CT volumes.

In this case, the alignment, performed by the motion stopping function 113, that the first regions are substantially at a same position, includes alignment that the set first regions are at the same position. Moreover, the alignment, performed by the motion stopping function 113, that the first regions are substantially at a same position, includes alignment that the placed regions of interest are at a same position even if a difference is found between the first regions included in the corresponding regions of interest.

In the following explanation, the first regions are multiple kinds of bone where a motion is made from the CT volumes in multiple time phases.

The motion stopping function 113 includes an extracting function 21, a setting function 22, an aligning function 23, a returning function 24, and a position changing function 25.

The extracting function 21 extracts pieces of 3D shadow region data (hereinafter called "3D shadow regions") in multiple time phases from the corresponding CT volumes, the 3D shadow regions each indicating a shadow region (a third region having a CT value not smaller than a threshold value). Each of the shadow regions is preferably binarized depending on whether a CT value in each of the CT volumes is not smaller than the threshold value.

Figure 4:
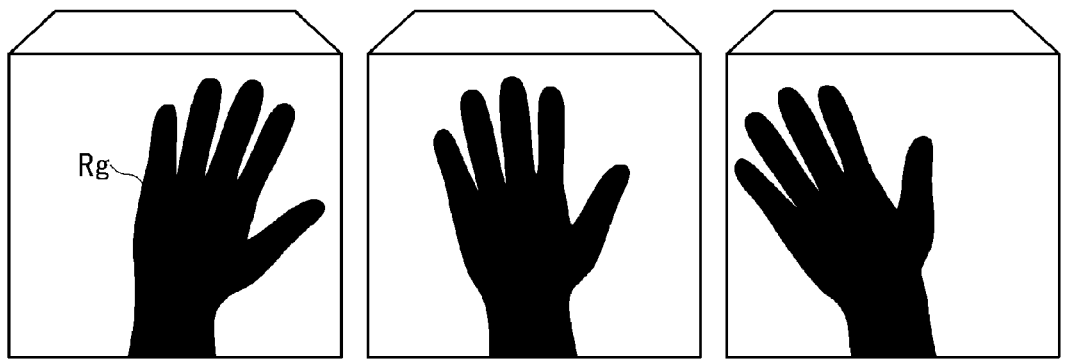
FIG. 4 is a diagram showing 3D shadow region data in three phases.

FIG. 4 is a diagram showing the 3D shadow regions in three phases. Each of the 3D shadow regions shown in FIG. 4 includes a shadow region Rg.

Referring to FIG. 2 again, the extracting function 21 may determine pieces of 3D surface data (polygon data) each indicating a skin shadow region (a CT value for skin being about −400[HU]), based on CT values in the each CT volume, and generate, as the 3D shadow regions each including the skin shadow region and an internal portion of the region. Each of the CT volumes has a CT value specific to each tissue, allowing the extracting function 21 to form an iso-surface having a CT value for skin. In the result, the extracting function 21 generates the pieces of the 3D surface data.

The setting function 22 detects pieces of first common shadow region data (hereinafter called "first common shadow regions") in multiple time phases from the 3D shadow regions by performing a differencing operation on the 3D shadow regions generated by the extracting function 21, the first common shadow regions being common in the 3D shadow regions. Subsequently, the setting function 22 deletes the first common shadow regions from the corresponding 3D shadow regions. In the result, the setting function 22 sets remaining non-common shadow regions as pieces of 3D non-common region data (hereinafter called "3D non-common regions") in multiple time phases.

The setting function 22 sets only the 3D non-common shadow regions included in the corresponding 3D shadow regions. In the result, the setting function 22 limits target regions for linear alignment by the aligning function 23 to the corresponding 3D non-common regions, the target regions being discussed later.

Figure 5:
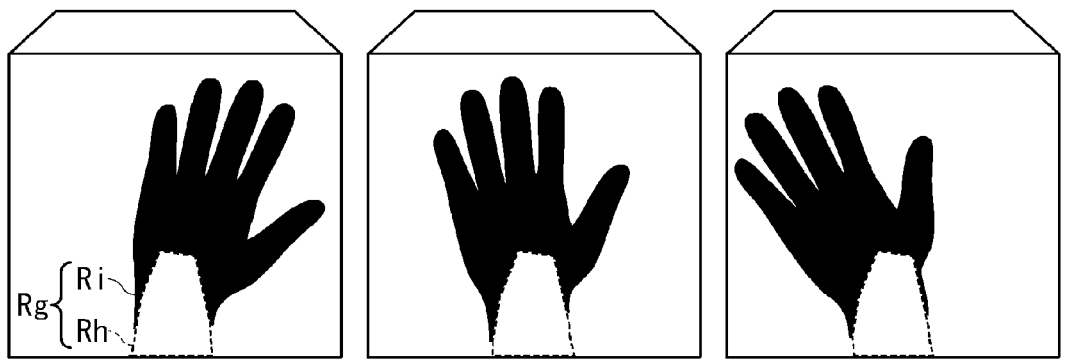
FIG. 5 is a diagram showing 3D non-common region data in three phases.

FIG. 5 is a diagram showing the 3D non-common regions in three phases. Each of the 3D non-common regions shown in FIG. 5 only shows a non-common shadow region Ri of the shadow region Rg without the first common shadow region Rh.

Referring to FIG. 2 again, the aligning function 23 defines one phase of the 3D non-common regions as a reference region, the 3D non-common regions being set by the setting function 22. The aligning function 23 linearly aligns each of the 3D non-commons with the defined reference region. In the result, the aligning function 23 generates pieces of 3D corrected region data (corrected medical image data) (hereinafter called "3D corrected regions") in multiple time phases.

Figure 6:
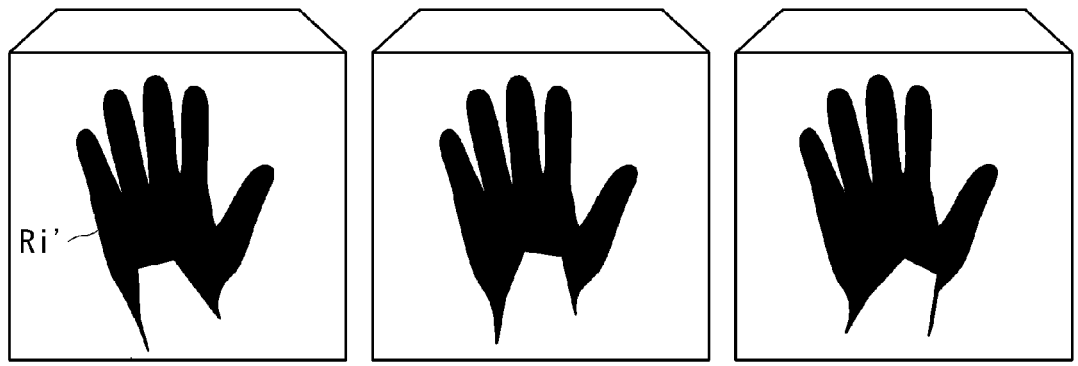
FIG. 6 is a diagram showing 3D corrected region data in three phases.

FIG. 6 is a diagram showing the 3D corrected regions in three phases. Each of the 3D corrected regions shown in FIG. 6 includes a non-common shadow region Ri' aligned with the non-common shadow region Ri (shown in FIG. 5).

Referring to FIG. 2 again, the returning function 24 calculates an amount of movement of each 3D corrected region generated by the aligning function 23. The returning function 24 changes positions of the first common shadow regions Rh (shown in FIG. 5) which are detected by the setting function 22, according to the corresponding amounts calculated. Subsequently, the returning function 24 returns first common shadow regions after the position changing to the corresponding 3D corrected regions. In the result, the returning function 24 generates pieces of 3D returned region data (hereinafter called "3D returned regions") in multiple time phases.

Figure 7:
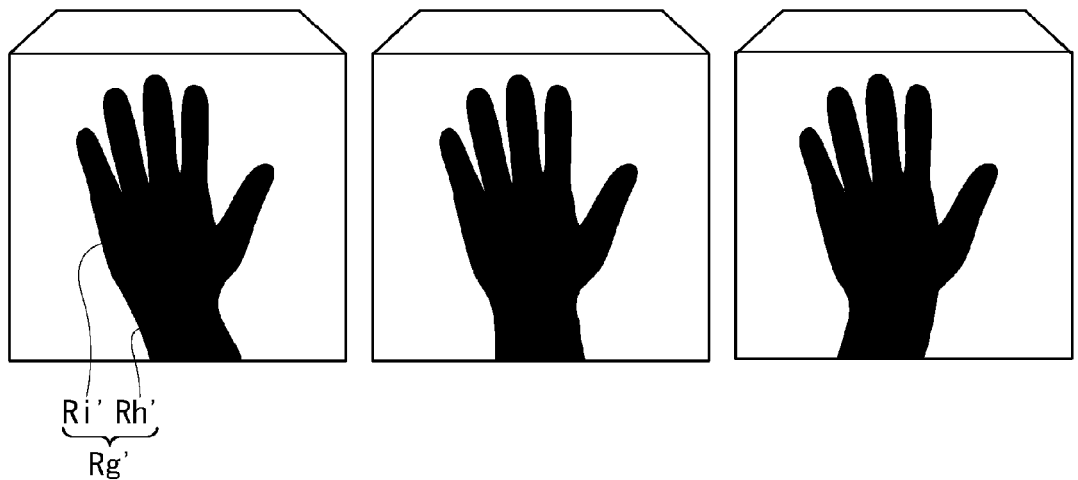
FIG. 7 is a diagram showing 3D returned region data in three phases.

FIG. 7 is a diagram showing the 3D returned regions in three phases. Each of the 3D returned regions shown in FIG. 7 includes a shadow region Rg' obtained by returning the first common shadow region after the position changing. The shadow region Rg' includes the non-common shadow region Ri' shown in FIG. 6 and a first common shadow region Rh' obtained by the change of the position.

Figure 8:
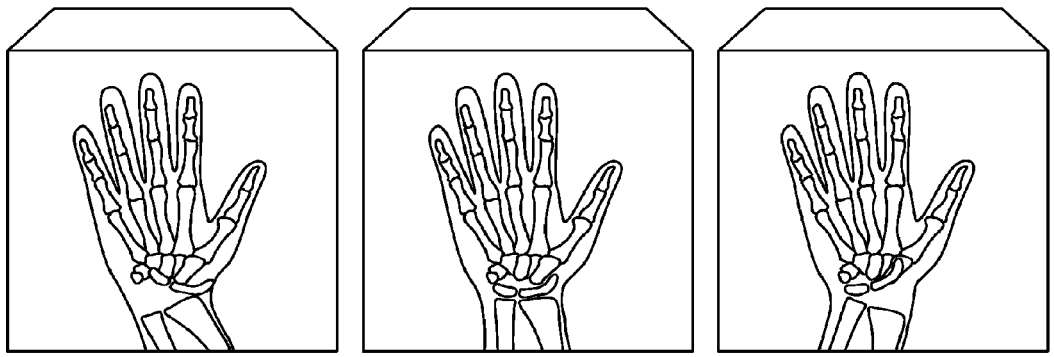
FIG. 8 is a diagram showing position changed volume data in three phases.

Referring to FIG. 2 again, the position changing function 25 calculates amounts of movement from the shadow regions Rg (shown in FIG. 4) to the corresponding shadow regions Rg' (shown in FIG. 7) of the corresponding 3D shadow regions. The position changing function 25 changes the positions of the CT volumes according to the corresponding the corresponding amounts calculated. In the result, the position changing function 25 generates pieces of position changed volume data (position changed volumes) in multiple time phases. FIG. 8 is a diagram showing the position changed volume in three phases.

Referring to FIG. 2 again, the display controlling function 114 generates 3D images (pieces of shaded volume rendering (SVR) image data, maximum intensity projection (MIP) image data, and multi planar reconstruction (MPR) image data) by rendering the position change volumes generated by the position changing function 25. The display controlling function 114 provides 4D representation (sequentially in multiple time phases) using the 3D images on the display 14.

Figure 9:
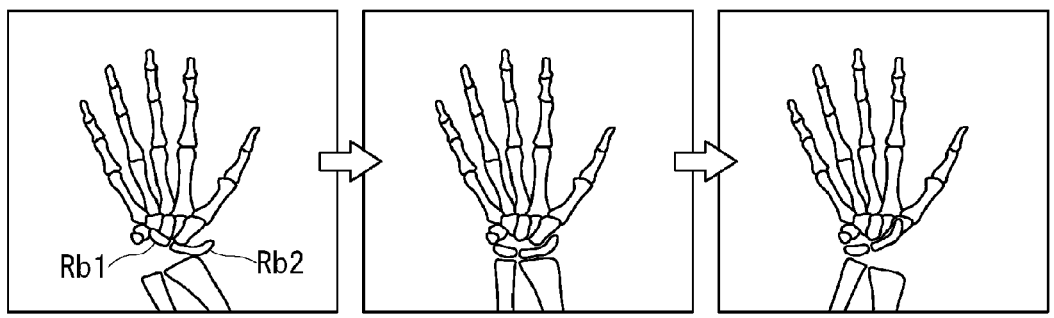
FIG. 9 is a diagram showing a first example of 4D representation.

FIG. 9 is a diagram showing a first example of 4D representation.

FIG. 9 shows the 4D representation example based on the 3D images.

As shown in FIG. 9, the 3D images used in the 4D representation include a stationary bone region and a moving bone region. The stationary bone region corresponds to a bone which does not have to attract attention in image diagnosis of a ligament. Specifically, as shown in FIG. 9, the motion of the bone which does not have to attract attention in image diagnosis of a ligament is fixed (locked) in 4D representation. In the example of FIG. 9, the 4D representation fixes motions of a distal phalanx, a middle phalanx, a proximal phalanx, a metacarpal bone, a hamate bone, a capitate bone, a trapezoid bone, a trapezium bone, a pisiform bone, and a triangular bone which do not have to attract attention in image diagnosis of a ligament.

The moving bone region in the 4D representation corresponds to a target bone to be noticed in image diagnosis of a ligament, and a bone (an ulna and a radius) which does not have to attract attention in image diagnosis of a ligament and is distinguishable from other bones in the 4D representation. In other words, as shown in FIG. 9, a target bone to be noticed in image diagnosis of a ligament is moved in the 4D representation. In the example of FIG. 9, the 4D representation moves a lunate bone Rb1, a navicular bone Rb2, an ulna and a radius. The lunate bone Rb1 and the navicular bone Rb2 are the target bones to be noticed in image diagnosis of a ligament. The ulna and the radius do not have to attract attention in image diagnosis of a ligament and are distinguishable from other bones in the 4D display.

Second Display Example

The returning function 24 shown in FIG. 2 may generate pieces of 3D common region data (hereinafter called "3D common regions") in multiple time phases by extracting common shadow regions (second common shadow regions) from the corresponding 3D returned regions (shown in FIG. 7).

Figure 10:
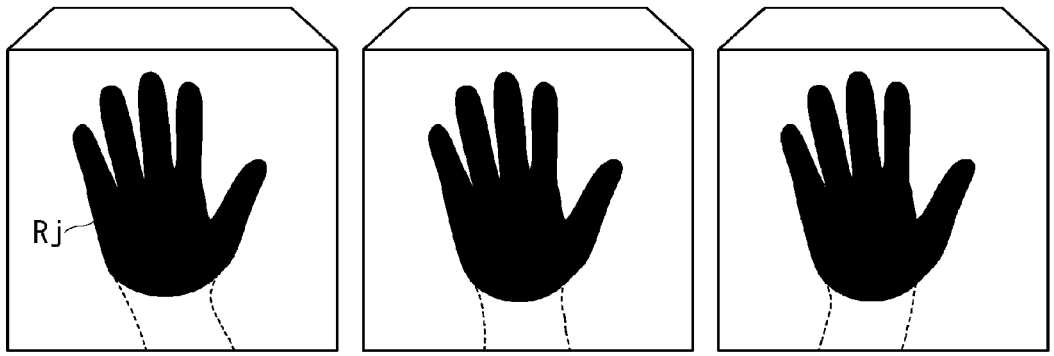
FIG. 10 is a diagram showing 3D common region data in three phases.

FIG. 10 is a diagram showing the 3D common regions in three phases. Each of the 3D common regions shown in FIG. 10 only includes a common shadow region Rj of the shadow region Rg' (shown in FIG. 7).

Figure 11:
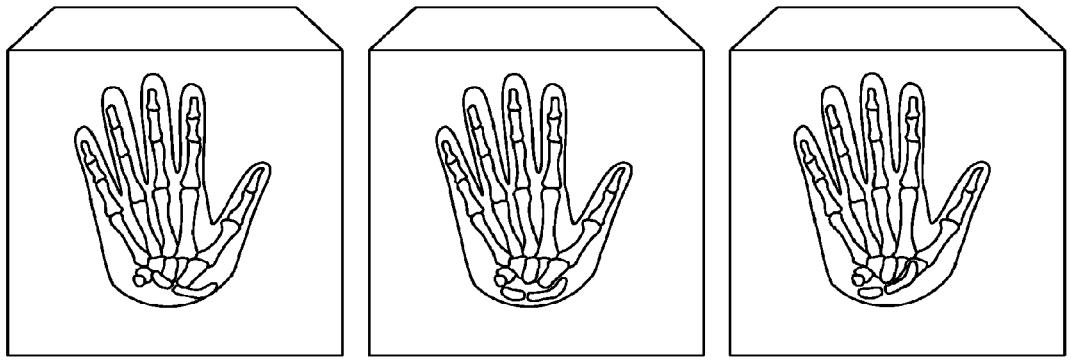
FIG. 11 is a diagram showing position changed volume data in three phases.

Referring to FIG. 2 again, the position changing function 25 calculates portions each corresponding to the common shadow region Rj (shown in FIG. 10) of a region (voxels) for the CT volume shown in FIG. 3. The position changing function 25 calculates each amount of movement from a portion corresponding to the common shadow region Rj (shown in FIG. 10) of the shadow region Rg (shown in FIG. 4) to the common shadow region Rj (shown in FIG. 10) of the corresponding 3D common region. The position changing function 25 changes each position of the calculated portion according to the calculated amount. In the result, the position changing function 25 generates position changed volumes. FIG. 11 is a diagram showing the position changed volume in three phases.

Referring to FIG. 2 again, the display controlling function 114 generates 3D images by rendering the position changed volumes generated by the position changing function 25. The display controlling function 114 provides 4D representation using the 3D images on the display 14.

Figure 12:
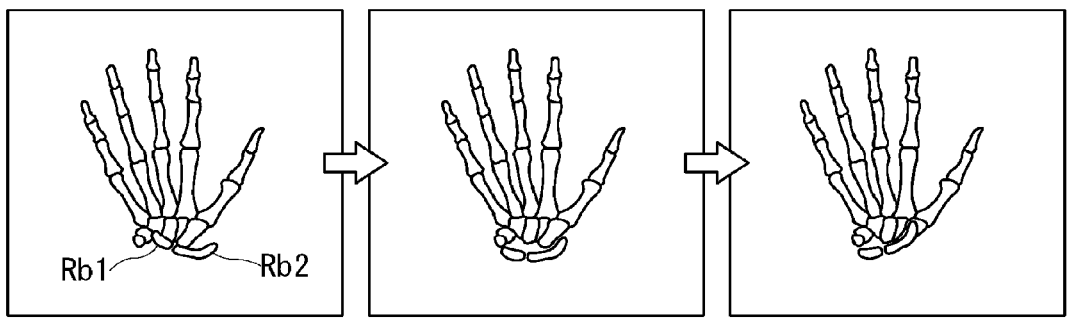
FIG. 12 is a diagram showing a second example of 4D representation.

FIG. 12 is a diagram showing a second example of 4D representation.

FIG. 12 shows a 4D representation example based on the 3D images and partially shows the 3D images shown in FIG. 9.

As shown in FIG. 12, the 3D images used in the 4D representation include a stationary bone and a moving bone. The stationary bone corresponds to a bone which does not have to attract attention in image diagnosis of a ligament. Specifically, as shown in FIG. 12, a motion of the bone which does not have to attract attention in image diagnosis of a ligament is fixed in 4D representation. In the example of FIG. 12, the 4D representation fixes motions of a distal phalanx, a middle phalanx, a proximal phalanx, a metacarpal bone, a hamate bone, a capitate bone, a trapezoid bone, a trapezium bone, a pisiform bone, and a triangular bone which do not have to attract attention in image diagnosis of a ligament.

The moving bone in the 4D representation corresponds to a target bone to be noticed in image diagnosis of a ligament. In other words, as shown in FIG. 12, the target bone to be noticed in image diagnosis of a ligament is moved in the 4D representation. In the example of FIG. 12, the 4D representation only moves the lunate bone Rb1 and the navicular bone Rb2 to be noticed in image diagnosis of a ligament.

Third Display Example

The display controlling function 114 shown in FIG. 2 specifies a second region moving in the corrected medical images. Specifically, the display controlling function 114 specifies the second region (bone region) moving in the position changed volumes (shown in FIG. 11). The display controlling function 114 sequentially displays the second bone regions on the display 14 in a display format where the second bone regions are distinguishable.

The display controlling function 114 performs nonlinear (non-rigid) alignment on the position changed volumes and defines regions each including changing voxels as the moving bone region. The display controlling function 114 defines one phase of the position changed volumes as a reference volume. The display controlling function 114 calculates an amount of nonlinear displacement of each position changed volume (e.g., volumes right after the corresponding reference volumes) other than the reference volume. The amount of nonlinear displacement can be expressed by a combination of translation and deformation movement. The display controlling function 114 extracts voxels having an amount of nonlinear displacement of at least a threshold value (exceeding the threshold value) as the second bone region, and defines the second bone regions as pieces of 3D specified bone region data (hereinafter called "3D specified bone regions") in multiple time phases. The display controlling function 114 generates 3D images by rendering the 3D specified bone regions. The display controlling function 114 provides 4D representation using the 3D images on the display 14.

Figure 13:
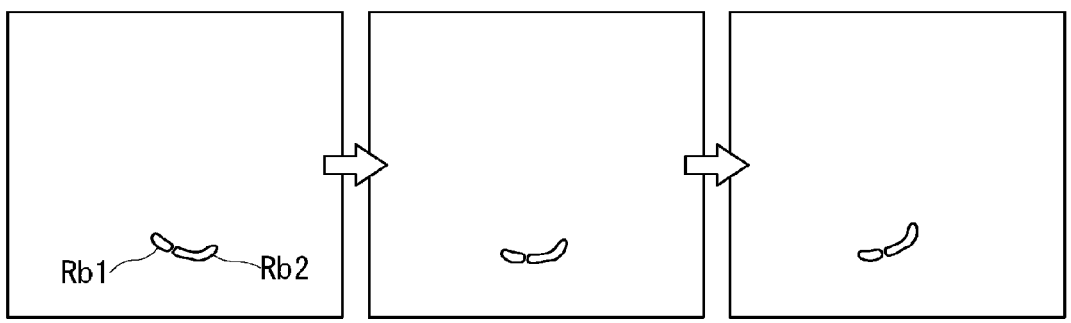
FIG. 13 is a diagram showing a third example of 4D representation.

FIG. 13 is a diagram showing a third example of 4D representation.

FIG. 13 shows the 4D representation example based on the 3D specified bone regions.

As shown in FIG. 13, the 3D images used in the 4D representation only include the second regions (bone regions). The second region which is the moving bone region in the 4D representation corresponds to a target bone to be noticed in image diagnosis of a ligament. Specifically, as shown in FIG. 13, the bone to be noticed in image diagnosis of a ligament is moved in the 4D representation. In the example of FIG. 13, only the lunate bone Rb1 and the navicular bone Rb2 to be noticed in image diagnosis of a ligament are moved in the 4D representation.

Fourth Display Example

As in the third display example, the display controlling function 114 shown in FIG. 2 specifies the second region (bone region) moving in the corrected medical images, and sequentially displays the second regions in a display mode where the second regions are distinguishable. The display controlling function 114 changes a voxel value of a voxel corresponding to each of the second regions included in the corresponding position changed volumes (shown in FIG. 8). The display controlling function 114 generates 3D images for easily recognizing the second regions.

The display controlling function 114 renders position changed volumes after the voxel value changing to generate 3D images. The display controlling function 114 provides 4D representation using the 3D images on the display 14.

Figure 14:
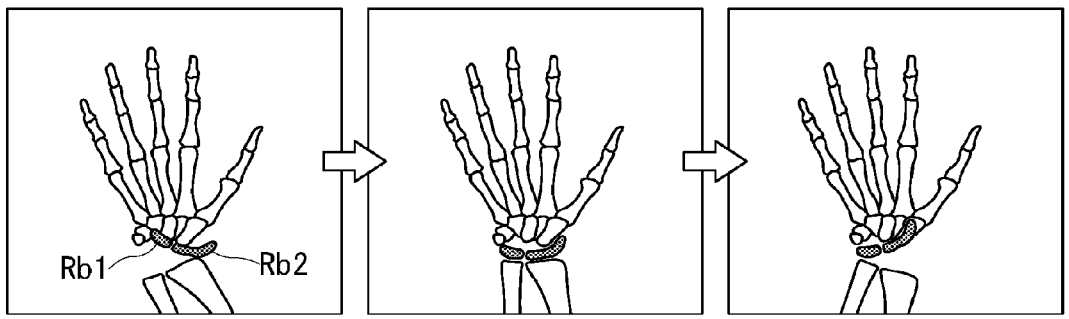
FIG. 14 is a diagram showing a fourth example of 4D representation.

FIG. 14 is a diagram showing a fourth example of 4D representation.

FIG. 14 shows a 4D representation example based on the 3D images each including mapping of the target bones Rb1 and Rb2 to be noticed in image diagnosis of a ligament in the 4D representation of FIG. 9.

As shown in FIG. 14, the target bones to be noticed in image diagnosis of a ligament are more easily recognized than bones which do not have to attract attention in image diagnosis of a ligament in 4D representation.

Fifth Display Example

As in the third and fourth display examples, the display controlling function 114 shown in FIG. 2 specifies the second region (bone region) moving in the corrected medical images, and sequentially displays the second regions on the display 14 in the display mode where the second regions are distinguishable. The display controlling function 114 changes a voxel value of a voxel corresponding to each of the second regions included in the corresponding position changed volumes (shown in FIG. 11). The display controlling function 114 generates 3D images for easily recognizing the second regions.

The display controlling function 114 renders the position changed CT volumes after the voxel value changing to generate 3D images. The display controlling function 114 provides 4D representation using the 3D images on the display 14.

Figure 15:
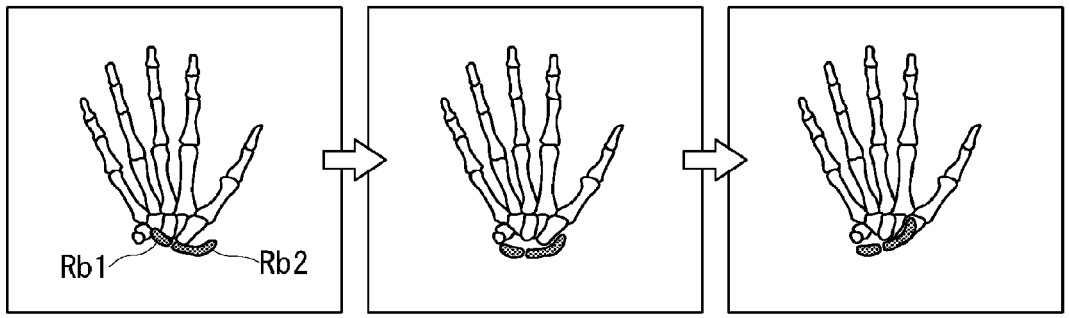
FIG. 15 is a diagram showing a fifth example of 4D representation.

FIG. 15 is a diagram showing a fifth example of 4D representation.

FIG. 15 shows a 4D representation example based on the 3D images each including mapping of the target bones Rb1 and Rb2 to be noticed in image diagnosis of a ligament in the 4D representation of FIG. 11.

As shown in FIG. 15, the target bones to be noticed in image diagnosis of a ligament are more easily recognized than bones which do not have to attract attention in image diagnosis of a ligament in 4D representation.

Specifically, the medical imaging apparatus 10 and the medical imaging method according to the present embodiment fixes, in 4D representation, a motion of the bone which does not have to attract attention in image diagnosis of a ligament and less recognizable, the bone being a part of overall bones. Thus, according to the medical imaging apparatus 10 and the medical imaging method of the present embodiment, there is no need for an operator to visually confirm a bone having abnormal motion while comparing the executed 4D representations. This reduces a burden on the operator so as to improve efficiency of operator's image diagnosis of ligaments.

Moreover, the medical imaging apparatus 10 and the medical imaging method according to the present embodiment stops a motion on the 3D data, enabling optional setting along a line of sight in 4D representation. This improves diagnosis efficiency for the operator.

(Modification)

The CT volumes are described as the medical images for a subject to be stopped. The motion stopping function 113 may generate pieces of CT-2D data (hereinafter called "CT-2Ds") in multiple time phases based on the corresponding CT volumes (shown in FIG. 3) and the CT-2Ds may serve as the medical images to be stopped.

Figure 16:
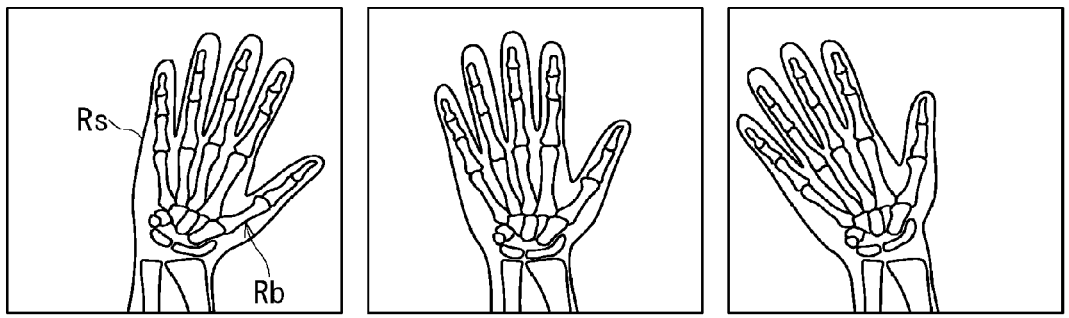
FIG. 16 is a diagram showing CT-2D data in three phases.

FIG. 16 is a diagram showing CT-2Ds in three phases. Each of the CT-2Ds shown in FIG. 3 roughly includes a bone region Rb indicating a bone shadow region and a skin region Rs indicating a skin shadow region.

Pieces of the MIP data (hereinafter called "MIPs") in multiple time phases serving as the CT-2Ds are pieces of 2D data each including pixels on a projection plane in a 2D array, the pixels each having a maximum CT value on a ray (a line orthogonal to the projection plane), the maximum CT value being obtained from the CT volumes. In other words, each of the MIPs is 2D data including 3D information. Thus, based on the MIPs, the display controlling function 114 can generate 3D bone regions with a window level (WL) substantially equivalent to a CT value for a bone, and can display the 3D bone regions as 3D images.

Specifically, the medical imaging apparatus 10 and the medical imaging method according to a modification of the present embodiment fixes, in 4D representation, a motion of the bone which does not have to attract attention in image diagnosis of a ligament and less recognizable, the bone being a part of overall bones. Thus, according to the medical imaging apparatus 10 and the medical imaging method of the modification of the present embodiment, there is no need for an operator to visually confirm a bone having abnormal motion while comparing the executed 4D representations. This reduces a burden on the operator so as to improve efficiency of operator's image diagnosis of ligaments.

The medical imaging apparatus and the medical imaging method according to at least one of the embodiments can improve image diagnosis efficiency for the operator.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical imaging apparatus, comprising:
processing circuitry configured to
obtain pieces of medical image data, the pieces each being generated in each of time phases and each including bone regions;
set a first bone region from the bone regions included in each of the pieces;
generate pieces of corrected medical image data by aligning the pieces of medical image data so that a plurality of the first bone regions are substantially at a same position;
specify a second bone region by analyzing the bone regions included in each of the pieces of the corrected medical image data, the second bone region corresponding to a bone moving in the pieces of the corrected medical image data; and
display a plurality of the second bone regions so as to be recognized on a display.

2. The medical imaging apparatus according to claim 1, wherein the processing circuitry is further configured to:
specify a third region included in each of the pieces of the medical image data, the third region having a voxel value in a predetermined threshold range; and
set the first bone region by comparing positions of the respective third regions.

3. The medical imaging apparatus according to claim 2, wherein the processing circuitry is further configured to set the first bone region by performing a differencing processing of the third regions.

4. The medical imaging apparatus according to claim 1, wherein the medical image data is CT data.

5. The medical imaging apparatus according to claim 2, wherein the processing circuitry is further configured to:
apply a binary operation to the pieces of the medical image data; and
specify voxels as the third region, the voxels each having a voxel value of at least a threshold value, and the voxels being included in each of the pieces of the medical image data.

6. The medical imaging apparatus according to claim 1, wherein the processing circuitry is further configured to:
obtain pieces of 3D corrected medical image data by aligning pieces of 3D medical image data as the pieces of the medical image data; and
specify a 3D second bone region as the second bone region, the 3D second bone region corresponding to the bone moving in the pieces of the 3D corrected medical image data.

7. The medical imaging apparatus according to claim 6, wherein the processing circuitry is further configured to display a plurality of the 3D second bone regions so as to be recognized on the display by three-dimensionally rendering processing the 3D second bone region.

8. The medical imaging apparatus according to claim 1, wherein the processing circuitry is further configured to:
obtain pieces of 2D corrected medical image data by aligning pieces of 2D medical image data as the pieces of the medical image data; and
specify a 2D second bone region as the second bone region, the 2D second bone region corresponding to the bone moving in the pieces of the 2D corrected medical image data.

9. The medical imaging apparatus according to claim 8, wherein the processing circuitry is further configured to display a plurality of the 2D second bone regions so as to be recognized on the display by maximum intensity projection (MIP) processing the 2D second bone region.

10. The medical imaging apparatus according to claim 1, wherein the processing circuitry is further configured to set at least one kind of bone as the first bone region.

11. The medical imaging apparatus according to claim 10, wherein the processing circuitry is further configured to set the first bone region in response to an input signal from input circuitry.

12. The medical imaging apparatus according to claim 1, wherein the processing circuitry is further configured to:
place a region of interest included in each of the pieces of the medical image data so as to set at least one kind of bone as the first bone region included in the corresponding region of interest; and
align the pieces of medical image data so that a plurality of the regions of interest are substantially at a same position.

13. The medical imaging apparatus according to claim 12, wherein the processing circuitry is further configured to set the region of interest in response to an input signal from input circuitry.

14. A medical imaging method, comprising:
obtaining pieces of medical image data, the pieces each being generated in each of time phases and each including bone regions;
setting a first bone region from among the bone regions included in each of the pieces;
generating pieces of corrected medical image data by aligning the pieces of medical image data so that a plurality of the first bone regions are substantially at a same position;
specifying a second bone region by analyzing the bone regions included in each of the pieces of the corrected medical image data, the second bone region corresponding to a bone moving in the pieces of the corrected medical image data; and
displaying a plurality of the second bone regions so as to be recognized on a display.

* * * * *